United States Patent
Kapoor et al.

(10) Patent No.: US 12,311,044 B2
(45) Date of Patent: May 27, 2025

(54) ANTIMICROBIAL COMPOSITION

(71) Applicant: CONOPCO, INC., Trumbull, CT (US)

(72) Inventors: Renu Kapoor, Bangalore (IN); Srikala Kumaran, Bangalore (IN); Mruthyunjaya Swamy Mathapathi, Bangalore (IN); Amitabha Majumdar, Bangalore (IN)

(73) Assignee: Conopco, Inc., Hoboken, NJ (US)

( * ) Notice: Subject to any disclaimer, the term of this patent is extended or adjusted under 35 U.S.C. 154(b) by 929 days.

(21) Appl. No.: 17/296,568

(22) PCT Filed: Nov. 26, 2019

(86) PCT No.: PCT/EP2019/082564
§ 371 (c)(1),
(2) Date: May 25, 2021

(87) PCT Pub. No.: WO2020/126347
PCT Pub. Date: Jun. 25, 2020

(65) Prior Publication Data
US 2022/0087914 A1    Mar. 24, 2022

(30) Foreign Application Priority Data
Dec. 18, 2018   (EP) .................... 18213528

(51) Int. Cl.
| | | |
|---|---|---|
| *A61K 8/41* | (2006.01) | |
| *A61K 8/34* | (2006.01) | |
| *A61K 8/49* | (2006.01) | |
| *A61Q 17/00* | (2006.01) | |
| *A61Q 19/10* | (2006.01) | |

(52) U.S. Cl.
CPC ............... *A61K 8/41* (2013.01); *A61K 8/347* (2013.01); *A61K 8/4926* (2013.01); *A61Q 17/005* (2013.01); *A61Q 19/10* (2013.01)

(58) Field of Classification Search
CPC ........ A61K 8/41; A61K 8/347; A61K 8/4926; A61Q 17/005; A61Q 19/10
See application file for complete search history.

(56) References Cited

U.S. PATENT DOCUMENTS

| | | | |
|---|---|---|---|
| 3,050,467 A | 8/1962 | Horowtiz et al. | |
| 3,907,745 A | 9/1975 | Bsharah et al. | |
| 4,585,597 A | 4/1986 | Lang et al. | |
| 5,532,290 A | 2/1996 | Newington et al. | |
| 6,080,391 A | 6/2000 | Tsuchiya et al. | |
| 6,632,422 B2 | 10/2003 | Burry et al. | |
| 7,347,985 B2 | 3/2008 | Maxwell et al. | |
| 8,071,077 B2 | 12/2011 | Subramanyam et al. | |
| 9,000,231 B2 | 4/2015 | Naik et al. | |
| 9,426,981 B2 * | 8/2016 | Hurtmanns | A01N 25/30 |
| 10,130,093 B2 | 11/2018 | Macinga et al. | |
| 10,251,392 B2 | 4/2019 | Karandikar et al. | |
| 2003/0161798 A1 | 8/2003 | Kellner et al. | |
| 2004/0116551 A1 | 6/2004 | Terry | |
| 2006/0047005 A1 | 3/2006 | Salamone | |
| 2006/0134020 A1 | 6/2006 | Robinson et al. | |
| 2006/0134024 A1 | 6/2006 | Trivedi et al. | |
| 2006/0264497 A1 | 11/2006 | Zeligs | |
| 2006/0275222 A1 | 12/2006 | James Dodds et al. | |
| 2007/0281999 A1 | 12/2007 | Fox et al. | |
| 2008/0000498 A1 | 1/2008 | Lestage et al. | |
| 2008/0014247 A1 | 1/2008 | Lu et al. | |
| 2008/0226582 A1 | 9/2008 | Park et al. | |
| 2008/0260869 A1 | 10/2008 | Faller et al. | |
| 2009/0156551 A1 | 6/2009 | Kilpert et al. | |
| 2010/0120911 A1 | 5/2010 | Majeed et al. | |
| 2011/0129426 A1 | 6/2011 | Tian et al. | |
| 2011/0150949 A1 | 6/2011 | Gonzales et al. | |
| 2012/0020896 A1 | 1/2012 | Trivedi et al. | |
| 2012/0208894 A1 | 8/2012 | Kampf | |
| 2012/0251464 A1 | 10/2012 | Subramanyam et al. | |
| 2012/0288548 A1 | 11/2012 | Boyd et al. | |
| 2013/0183394 A1 | 7/2013 | Wuttke | |
| 2014/0234232 A1 | 8/2014 | Subramanyam et al. | |
| 2014/0328772 A1 | 11/2014 | Hourigan | |
| 2015/0079141 A1 | 3/2015 | Wingfield | |
| 2015/0157542 A1 | 6/2015 | Schaeffer | |

(Continued)

FOREIGN PATENT DOCUMENTS

| | | |
|---|---|---|
| CN | 1331968 | 1/2002 |
| CN | 101002798 | 7/2007 |
| CN | 101279901 | 10/2008 |
| CN | 101804043 | 8/2010 |
| CN | 102743363 | 4/2011 |
| CN | 102716188 | 10/2012 |
| CN | 102871989 | 1/2013 |
| CN | 103045400 | 4/2013 |

(Continued)

OTHER PUBLICATIONS

Mathapathi et al. "Niacinamide leave-on formulation provides long-lasting protection against bacteria in vivo". Experimental Dermatology. 26(9):827-829. (Year: 2017).*

(Continued)

*Primary Examiner* — Jeffrey S Lundgren
*Assistant Examiner* — Ibrahim D Bori
(74) *Attorney, Agent, or Firm* — Krista J. Aiello

(57) ABSTRACT

The present invention relates to an antimicrobial composition. More particularly the present invention relates to an antimicrobial composition for malodor and oral biofilm inhibitions benefits. Accordingly, the present invention provides an antimicrobial composition comprising: a. 0.1 to 10% by weight of tetrahydroxypropyl ethylenediamine (THPE) and, b. 0.001 to 10% by weight of at least one compound selected from a biphenol.

13 Claims, No Drawings

(56) References Cited

U.S. PATENT DOCUMENTS

| | | | |
|---|---|---|---|
| 2017/0044313 | A1 | 2/2017 | Youssef |
| 2017/0080197 | A1 | 3/2017 | Paunescu et al. |
| 2017/0113989 | A1 | 4/2017 | Jaracz et al. |
| 2017/0173162 | A1 | 6/2017 | Jiao et al. |
| 2019/0117569 | A1 | 4/2019 | Epps et al. |
| 2020/0330408 | A1 | 10/2020 | Appavoo et al. |

FOREIGN PATENT DOCUMENTS

| | | | | |
|---|---|---|---|---|
| CN | 104920489 | | 9/2015 | |
| CN | 105198712 | | 12/2015 | |
| CN | 105997659 | | 10/2016 | |
| CN | 106358648 | | 2/2017 | |
| CN | 106924120 | | 7/2017 | |
| CN | 109771312 | | 10/2023 | |
| DE | 202004006865 | | 12/2004 | |
| DE | 102007028508 | | 4/2008 | |
| DE | 202010006005 | | 7/2010 | |
| DE | 102010015788 | | 10/2011 | |
| EP | 2272339 | | 1/2011 | |
| EP | 2589374 | | 5/2013 | |
| EP | 2589375 | | 5/2013 | |
| EP | 3246022 | | 11/2017 | |
| JP | 2007161651 | | 6/2007 | |
| JP | 2008247775 | | 10/2008 | |
| JP | 2011111444 | | 6/2011 | |
| KR | 20150041981 | | 4/2015 | |
| WO | WO0001353 | | 1/2000 | |
| WO | WO0047184 | | 8/2000 | |
| WO | WO0182922 | | 11/2001 | |
| WO | WO0185116 | | 11/2001 | |
| WO | WO02091846 | | 11/2002 | |
| WO | WO2006026170 | | 3/2006 | |
| WO | WO2006071653 | | 7/2006 | |
| WO | WO2006071655 | | 7/2006 | |
| WO | WO2006071654 | | 9/2006 | |
| WO | WO2006101818 | | 9/2006 | |
| WO | WO2006101864 | | 9/2006 | |
| WO | WO2009101615 | | 8/2009 | |
| WO | WO2010090855 | | 8/2010 | |
| WO | WO11038797 | | 7/2011 | |
| WO | WO2011106003 | | 9/2011 | |
| WO | WO2011106493 | | 9/2011 | |
| WO | WO2012002945 | | 1/2012 | |
| WO | WO2012015408 | | 2/2012 | |
| WO | WO2012084164 | | 6/2012 | |
| WO | WO2012087289 | | 6/2012 | |
| WO | WO2013036229 | | 3/2013 | |
| WO | WO2013081627 | | 6/2013 | |
| WO | WO2013089716 | | 6/2013 | |
| WO | WO2013095361 | | 6/2013 | |
| WO | WO2013095364 | | 6/2013 | |
| WO | WO2014092747 | | 6/2014 | |
| WO | 092014 | | 9/2014 | |
| WO | WO-2014131191 | A1 * | 9/2014 | ........... A61K 36/575 |
| WO | WO2015117957 | | 8/2015 | |
| WO | WO2015123115 | | 8/2015 | |
| WO | WO2016071827 | | 5/2016 | |
| WO | WO2017011665 | | 1/2017 | |
| WO | WO2017083363 | | 5/2017 | |
| WO | WO2017194256 | | 11/2017 | |
| WO | WO2019121319 | | 6/2019 | |
| WO | WO2020083737 | | 4/2020 | |
| WO | WO2021249760 | | 12/2021 | |
| WO | WO20203030963 | | 3/2023 | |
| WO | WO2023151986 | | 8/2023 | |

OTHER PUBLICATIONS

Guo-Ying Zuo et al.; In vitro synergism of magnolol and honokiol in combination with antibacterial agents against clinical isolates of methicillin-resistant *Staphylococcus aureus* (MRSA); BMC Complementary and Alternative Medicine; 2015; pp. 1-10; 15:425.

Lai Wah Chan et al.; Antimicrobial and antioxidant activities of Cortex Magnoliae Officinalis and some other medicinal plants commonly used in South-East Asia; Chinese Medicine; Nov. 28, 2008; pp. 1-10; 3:15; BioMed Central.

Greenberg et al.; Compressed Mints and Chewing Gum Containing Magnolia Bark Extract Are Effective against Bacteria Responsible for Oral Malodor; Journal of Agricultural and Food Chemistry; Oct. 20, 2007; 9465-9469; 55; American Chemical Society.

Guangjing Wufu; New Cosmetics Science; China Light Industry Press; Apr. 30, 1996; pp. 442-443, with English translation.

Anonymous; Novel Acne Cleansing and conditioning Lotion; Dr. Wu; Jul. 28, 2017; https://www.cosdna.com/chs/cosmetic_91f8301224.html; Cosdna.

GNPD Database (Online) Mintel; Sensitive Foam for Vulvovaginal Care; Procare Health Palomacare Espuma; Oct. 2015; pp. 1-6, with English translation, Record ID 3437909; Spain.

Notice of Opposition in EP18825643 (EP3727300); Jul. 28, 2023; with English translation; European Patent Office (EPO).

Stichwort: Benzalkoniumchlorid; Worterbuch der Kosmetik; 2004; pp. 1-3; with English translation.

Bin Liu; In vivo metabolism and analysis of traditional Chinese medicine ingredients; China Press of Traditional Chinese Medicine; Aug. 2011; p. 372, with English translation.

Drugbank Online; Dimethicone 100; 2022; pp. 1, Retrieved from Internet URL:https://go.drugbank.com/salts/DBSALT001523.

Poivre et al.; Biological activity and toxicity of the Chinese herb Magnolia officinalis Rehder & E. Wilson (Houpo) and its constituents; Biomed & Biotechnol; Mar. 2017; pp. 194-214; 18(3); J Zhejiang Univ-Sci B.

Luo et al.; Antifungal activity and potential mechanism of magnoflorine against Trichophyton rubrum; The Journal of Antibiotics; Oct. 20, 2020; pp. 206-214; 74; Japan Antibiotics Research Association; Japan.

Chemicalbook, Amphoteric surfactants; Chemical Products List; 2016; pp. 1-2, Retrieved from the Internet. https://www.chemicalbook.com/ProductCatalog_EN/1813.htm#:~:text=The%20lecithin%20%5B1%5D%20contained%20in,excellent%20emulsifying%20properties%20of%20oil.

Matsui, Hideo et al.; Synthesis and electronic behaviours of alternating indium-organic moiety binary hybrid copolymer; Databse Caplus (Online); 2006; pp. 1-2; XP002778749; Chemical Abstracts Service; United States of America.

Glidewell, Christopher et al.; Supramolecular chemistry of amine-phenol adducts; novel three-dimensional framework structures in adducts of bis . . . ; Database Caplus (Online); 2000; pp. 1-2; XP002778750; Chemical Abstracts Service; United States of America.

Goldberg, David P et al.; A decanuclear mixed-valent manganese complex with a high spin multiplicity in the ground state; Database Caplus (Online); 1993; pp. 1-3; XP002778751; Chemical Abstracts Service; United States of America.

Search Report and Written Opinion in EP17209949; Mar. 19, 2018; European Patent Office (EPO).

Search Report and Written Opinion in EP18202218; Dec. 19, 2018; European Patent Office (EPO).

Search Report and Written Opinion in PCTEP2018084749; Jan. 21, 2019; World Intellectual Property Org. (WIPO).

Search Report and Written Opinion in PCTEP2018085103; Jan. 31, 2019; World Intellectual Property Org. (WIPO).

Search Report and Written Opinion in EP17210127; May 4, 2018; European Patent Office (EPO).

Search Report and Written Opinoin in EP18213528; Jul. 19, 2019; European Patent Office (EPO).

Search Report and Written Opinoin in PCTEP201907817; Dec. 13, 2019; World Intellectual Property Org. (WIPO).

Search Report and Written Opinoin in PCTEP2019082564; Jan. 15, 2020; World Intellectual Property Org. (WIPO).

IPRP2 in PCTEP2018084749; May 13, 2020; World Intellectual Property Org. (WIPO).

IPRP1 in PCTEP2018085103; Jun. 23, 2020; World Intellectual Property Org. (WIPO).

GNPD Mintel; White Sunscreen; DHC; Jul. 2003; pp. 1-2, Record ID 214176; Japan.

(56) References Cited

OTHER PUBLICATIONS

GNPD Mintel; Eye Care; Martina Gebhardt Naturkosmetik; Nov. 2013; pp. 1-4, Record ID 2243030; Netherlands.
GNPD Mintel; Happy Aging Body Lotion; Martina Gebhardt Naturkosmetik; Feb. 2013; pp. 1-2, Record ID 1999361; Germany.
GNPD Mintel; Sheabutter Body Lotion; Martina Gebhardt Naturkosmetik; Feb. 2013; pp. 1-2, Record ID 1999393; Germany.
GNPD Mintel; Hand & Nail Hand Lotion; Martina Gebhardt Naturkosmetik; Feb. 2014; pp. 1-3, Record ID 2273913; Germany.
GNPD Mintel; Summer Time Face & Body Aftersun; Martina Gebhardt Naturkosmetik; Jul. 2015; pp. 1-3, Record ID 3058213; Germany.
Gnpd Mintel; Summer Time Face & Body Lotion; Martina Gebhardt Naturkosmetik; Jul. 2015; pp. 1-3, Record ID 3058215; Germany.
GNPD Mintel; Ginseng Cream; Martina Gebhardt Naturkosmetik; Feb. 2016; pp. 1-4, Record ID 3755787; Germany.
GNPD Mintel; Tassilo Linde; Martina Gebhardt Naturkosmetik; Jul. 2016; pp. 1-4, Record ID 4171881; Germany.
GNPD Mintel; Eye Care Fluid; Martina Gebhardt Naturkosmetik; Jun. 2017; pp. 1-3, Record ID 4855347; Germany.
Anonymous; Emergence EXO Serum Intensive; The Skin Saint; PP1, https://theskinsaint.com/products/emergence☐exo☐serum☐intensive.
GNPD Mintel; Day Cream SPF 10; Oriflame Optimals Vital Definition; May 2014; pp. 1-3, Record ID 2433677; Greece.
GNPD Mintel; Swiss Allure Skrab dlya Litsa (Exfoliating Gentle Peeling); Medena; Feb. 2017; pp. 1-2, Record ID 4594303; Russian Federation.
Anonymous; Vinoderm Gentle Peeling; Hair-France.fr; pp. 1-2, https://www.hair☐france.fr/fr/cleansing/792☐791☐creme☐gommante☐vinoderm.html; .; France.
Written Opinion 2 in PCTEP2019078179; Oct. 16, 2020; World Intellectual Property Org. (WIPO).
IPRP2 in PCTEP2019078179; Jan. 29, 2021; World Intellectual Property Org. (WIPO).
G. Kampf; Journal of Hospital Infection; Efficacy of ethanol in viruses in hand disinfection; Apr. 1, 2018; pp. 331-338; XP055714645; vol. 98, No. 4; Elsevier Ltd; Netherlands.
Malik et al.; AJIC: American Journal of Infection Control; Comparative efficacy of ethanol and isoprpanol against feline calicivirus, a norovirus surrogate; Feb. 1, 2006; pp. 31-35; XP005442120; vol. 34 No 1; Elsevier; Netherlands.
WR Moorer; Anitiviral activity of alcohol for surface disinfection; International Journal of Dental Hygiene; Jan. 1, 2003; pp. 138-142, XP055834836; vol. 1, No. 1; Blackwell Munksgaard; Netherlands.
Diphenyl; National Institute for Occupational Safety and Health; 2019; pp. 1-3.
Search Report and Written Opinion in EP23213180; May 8, 2024; European Patent Office (EPO).
Stephen M. Mudge; Fatty Alcohols—a review of their natural synthesis and environmental distribution; Nov. 2005; pp. 1-153; The Soap and Detergent Association.
Search Report and Written Opinion in EP24150487; Jun. 25, 2024; European Patent Office (EPO).
GNPD Database (Online) Mintel; Brightening Under Eye Gel; Simple Protect 'n' Glow; Nov. 2023; pp. 1-4, Record ID 11299696, XP093171437; India.
GNPD Database (Online) Mintel; White Cloud Spot Corrector; Skyn Iceland; Jan. 2013; pp. 1-6, Record ID 1966690, XP093171340; United Kingdom.
GNPD Database (Online) Mintel; Anti-Aging Daily Serum 2.0; Elizabeth Arden Prevage; Mar. 2021; pp. 1-7, Record ID 8553989, XP093171361; United Kingdom.
GNPD Database (Online) Mintel; Whitening Morning Yogurt; Naruko Raw Job's Tears Supercritical CO2; Nov. 2011; pp. 1-6, Record ID 1663269, XP093171456; Singapore.
Shen Zhengyi et al.; Hospital Infection Diseases, Part 2; China Medical Science and Technology Press; Apr. 2007; pp. 1442 with English translation; 1st edition, 1st printing; China.

\* cited by examiner

ANTIMICROBIAL COMPOSITION

CROSS REFERENCE TO RELATED APPLICATIONS

The present application is a U.S. National Phase Application under 35 U.S.C. § 371 of International Application No. PCT/EP2019/082564, filed on Nov. 26, 2019, which claims priority to European Patent Application No. 18213528.5, filed on Dec. 18, 2018, the contents of which are incorporated herein in their entireties.

FIELD OF THE INVENTION

The present invention relates to an antimicrobial composition. More particularly the present invention relates to antimicrobial composition for malodor and oral biofilm inhibitions benefits.

BACKGROUND OF THE INVENTION

People try to take good care of the external surfaces of their body as well as those of their pets to enable overall good health. Specific skin related issues that people care about include, good skin health free of infections, good skin tone and adequate moisturization. Oral cavity is another external surface that people try to take active care to maintain. They prefer their oral cavity including the gums and teeth to be free of problems like cavities, tartar, gingivitis, caries, bad breath also known as halitosis and plaque. Typically, people are also concerned with hair and scalp care. They generally prefer to have thick and long hair with minimum hair fall. Dandruff is a commonly occurring scalp problem for which a fungal microorganism has been implicated.

A good health for external surfaces including skin, oral cavity and scalp care are typically achieved by keeping them free of infections. One way to tackle infections is to treat it using antimicrobials after the infection has set in. Another approach is to leave a minimal amount of antimicrobial composition on the surface like e.g. skin of the hands, so that any invading microorganisms like e.g. bacteria are killed or inactivated so as to minimize spread of disease. Some bacteria like *Escherichia coli* (*E. coli*) and *Staphylococcus aureus* (*S. aureus*) are commonly found on the human skin. These bacteria per se do not trigger a pathogenic effect whilst commonly present on the skin. However, when they enter the human body through cuts on the skin and through acts like ingestion, these bacteria become pathogenic. Therefore, keeping the external surface of the body like e.g. hand and scalp, free of bacteria helps in preventing them from entering the human body thereby achieving the desired hygiene. Moreover, presence of certain microorganisms e.g. *Staphylococcus hominis* (*S. hominis*) with the biproduct of skin e.g. sebum produces malodor which is not desirable.

In the same way external surface like oral surface also amenable to problems like cavities, tartar, gingivitis, caries, and bad breath, also known as halitosis, and plaque. One of the starting point or main cause of the above mentioned oral problems is biofilm formation on teeth. This biofilm growth is fostered in presence of microbes e.g. bacteria.

There are various antimicrobial composition disclosed in the art.

U.S. Pat. No. 3,050,467 (Horowitz et al. 1962) discloses an antimicrobial cleansing composition consisting essentially of a mixture of a water-soluble soap and a silver salt of partially depolymerized alginic acid. The composition provides synergistic antimicrobial activity.

US2008014247A (Lu et al., 2008) discloses a composition having metal containing material, stearic acid and a pharmaceutically acceptable carrier to treat conditions caused by gram-positive, gram-negative, fungal pathogens and/or antibiotic-resistant bacteria. It further provides a method for inhibiting biofilm proliferation. The metal containing material can be silver.

WO0182922 (Procter and Gamble, 2001) discloses oral compositions comprising an effective amount of a polyphenol herbal extract selected from the group consisting of magnolol, honokiol, tetrahydromagnolol, tetrahydrohonokiol, and mixtures thereof; an effective amount of a buffering agent; from about 40 percent to about 99 percent of one or more aqueous carriers; wherein the oral composition has a total water content of from about 5 percent to about 70 percent.

US2009156551 (DSM, 2009) discloses compositions comprising magnolol and honokiol wherein the mol ratio of magnolol to honokiol is less than 0.6 as well as to the use of these compositions as medicament, in particular as a medicament for the treatment, co-treatment or prevention of inflammatory disorders.

Despite efforts thus far, people are always on a look out for new technologies e.g. actives or combination of actives that delivers improved antimicrobial benefit. Further, it is preferred if minimal amounts of known antimicrobial actives are used as people nowadays prefer minimum exposure to chemical ingredients. Therefore, antimicrobial compositions and actives that deliver an antimicrobial benefit, remains a topic of interest.

Need therefore exists to provide an antimicrobial composition comprising one or more actives that delivers an improved antimicrobial benefit. Need also exists to provide antimicrobial composition that comprises minimal amount of known antimicrobial actives to fight against malodor and biofilm formation.

It is therefore an object of the present invention to provide an antimicrobial composition.

It is another object of the present invention to provide an antimicrobial composition for providing effective protection against malodor.

It is yet another object of the present invention to provide an antimicrobial composition for providing effective protection against biofilm formation in oral surface.

The present inventors have surprisingly found out that a combination comprises a particular amount of tetrahydroxypropyl ethylenediamine (THPE) and a biphenol provides synergistic antimicrobial benefit and thereby satisfying one or more of the above said objects.

SUMMARY OF THE INVENTION

Accordingly, in a first aspect there is provided an antimicrobial composition comprising;
   a. 0.1 to 10% by weight of tetrahydroxypropyl ethylenediamine (THPE); and,
   b. 0.001 to 10% by weight of at least one compound selected from a biphenol.

In a second aspect there is provided a method of disinfecting a surface comprising the step of applying on to the surface a composition of the first aspect.

In a third aspect there is provided use of the composition of the first aspect for obtaining an antimicrobial benefit.

These and other aspects, features and advantages will become apparent to those of ordinary skill in the art from a reading of the following detailed description. For the avoidance of doubt, any feature of one aspect of the present invention may be utilized in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

The composition of the present invention intended for topical application including oral surface. The most preferred application of the composition is as an antimicrobial composition. Antimicrobial composition as mentioned herein above preferably means any composition, which is capable of killing or at least cause substantial reduction of the common disease causing and or foul smell causing microbes. The common disease causing gram-positive organisms includes *Staphylococcus, Streptococcus* and *Enterococcus* spp. Some of common disease causing gram-negative organisms includes *Escherichia coli, Salmonella, Klebsiella* and *Shigella*. *Escherichia coli* and *Salmonella* can cause severe gastrointestinal illnesses. One of the foul smell causing bacterial exist on human skin is *S. hominis*.

The present invention provides an antimicrobial composition comprising;
a. 0.1 to 10% by weight of tetrahydroxypropyl ethylenediamine (THPE); and,
b. 0.001 to 10% by weight of at least one compound selected from a biphenol.

Tetrahydroxypropyl Ethylenediamine (THPE)

The composition of the present invention comprises 0.1 to 10% by weight of tetrahydroxypropyl ethylenediamine (THPE). The preferred concentration of THPE is 0.1 to 8%, more preferably 0.1 to 5% and furthermore preferably 0.5 to 3% and most preferably 0.5 to 2%. Not wishing to be bound by theory it is stated lower amount of THPE is preferred because of processing ease. It is found that higher concentration of THPE in the formulation makes it difficult for processing. Higher amount of THPE also adversely affect the sensory of the resultant formulation.

The structure of THPE is as follows:

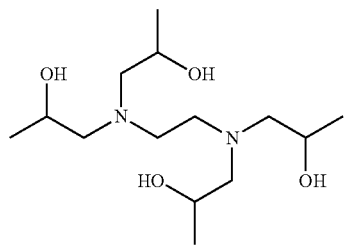 [SMILES: CC(O)CN(CCN(CC(C)O)CC(C)O)CC(C)O]

It is also known as N,N,N',N'-Tetrakis(2-hydroxypropyl) ethylenediamine or Quadrol. THPE generally used as emulsion stabilizer, dispersing agent, chelating agent in personal care formulations and as a solvent.

Biphenol

The composition of the present invention also comprises 0.001 to 10% by weight of at least one compound selected from a biphenol. Examples of biphenol that are suitable for use in the present invention include 2,4'-biphenol (IUPAC name: 2,4'-Dihydroxybiphenyl), 2,2'-biphenol (2,2'-Dihydroxybiphenyl), 3,3'-biphenol (3,3'-Dihydroxybiphenyl), 4,4'-biphenol (4,4'-Dihydroxybiphenyl), and mixtures thereof.

Preferably, the biphenol is a diallylbiphenol. This means the biphenol comprises diallyl substitution. The diallyl substitution may be present at any of the positions on biphenol structure. The preferred diallylbiphenol is a (5-3'-diallyl) biphenol or a (5-5'-diallyl)biphenol. The most preferred diallylbiphenol is a (5-3'-diallyl) biphenol.

The most preferred biphenol are selected from honokiol and/or magnolol.

Preferably, the composition comprises from 0.001 to 10%, preferably from 0.005 to 8%, more preferably from 0.01 to 6%, even more preferably from 0.05 to 5%, furthermore preferably from 0.1 wt to 4%, still more preferably from 0.5 to 3% and yet more preferably from 1 to 1.5% by weight of a biphenol.

We have found that the composition of the present invention i.e. the combination of tetrahydroxypropyl ethylenediamine (THPE) and at least one compound selected from a biphenol provides synergistic antimicrobial action. The antimicrobial action of two or more active compounds is considered additive if the combined action merely results from the addition of the effects the individual components would have in isolation. In contrast, the antimicrobial action of two or more active compounds is considered to be synergistic if the combined effect of the two or more compounds is stronger than expected based on the assumption of additivity. Without wishing to be bound by theory, it is believed that the antimicrobial action of the one compound may be enhanced by the action of the other compound and vice versa. Such enhancement may for instance originate from cooperative interplay between the mechanisms of antimicrobial action at the molecular level. Such enhanced antimicrobial action may manifest itself for instance by the fact that lower concentrations of active compounds are required to obtain complete microbial kill, or alternatively, that the same extent of microbial kill is arrived at in a shorter time. Whether an antimicrobial composition comprising two or more active compounds is capable of synergistic antimicrobial action may for instance be determined following the procedures and using the criteria as outlined in examples section below. Typically, evidence of synergistic antimicrobial action may be provided at concentrations below the minimum biocidal concentrations of each of the components when taken individually. However, it is generally believed that synergistic action can still occur when the concentration of one or more of the active compounds is raised above its minimum biocidal concentration (when taken individually).

The composition of the present invention also preferably comprises niacinamide or its derivatives. Niacinamide or Nicotinamide or Vitamin $B_3$ is a known molecule widely used as a skin lightening agent. The derivatives of niacinamide also encompasses any analogues of niacinamide. The preferred derivatives or analogues are picolinamide, isonicotinamide, N-cyclopropyl nicotinamide, and N-cyclopentyl nicotinamide.

The amount of niacinamide or its derivatives preferably in the range of 0.1 to 10%, more preferably 0.5 to 8%, furthermore preferably in the range of 1 to 5% and most preferably 1 to 3% by weight.

The composition of the present invention also comprises a cosmetically accepted base for delivering the product. The cosmetically acceptable base is preferably in the form of a cream, lotion, gel or emulsion.

The compositions may be prepared using different cosmetically acceptable emulsifying or non-emulsifying base. A highly suitable base is a cream. Vanishing creams are especially preferred. Vanishing cream bases generally comprise a mixture of fatty acid and soap. Vanishing cream base gives a highly appreciated matty feel to the skin. C12 to C20 fatty acids are especially preferred in vanishing cream bases, furthermore preferred being C14 to C18 fatty acids. Most preferably, the fatty acids are stearic acid or palmitic acid or mixtures thereof. The fatty acid is often hystric acid which is substantially (generally from 90 to 95% by weight) a mixture of 45% stearic and 55% palmitic acid. Thus, inclusion of hystric acid and its soap to prepare compositions of the invention is within the scope of the present invention. The fatty acid in the composition is preferably present in an amount from 5 to 20%, more preferably from 6 to 19% and even more preferably from 7 to 17% by weight of the composition. Soaps in the vanishing cream base include alkali metal salt of fatty acids, like sodium or potassium salts, most preferred being potassium stearate. The soap in the vanishing cream base is generally present in an amount in the range from 0.1 to 10%, more preferably from 0.1 to 3% by weight of the composition. Generally, the vanishing cream base topical compositions are prepared by taking a desired amount of total fatty matter and mixing with potassium hydroxide in desired amounts. The soap is usually formed in-situ during the mixing.

An especially suitable cosmetically acceptable base is one which comprises a water-in-oil emulsion comprising silicone oils as the continuous phase. The water-in-oil emulsions preferably comprise a cross-linked silicone elastomer blend.

Inclusion of silicone elastomer blend in a water-in-oil emulsion may be used as the cosmetically acceptable base for preparing the compositions of the present invention. While silicone fluids may be used, silicone elastomers which are cross-linked, are especially preferred. In contrast to silicone fluid polymers, the physical properties of elastomers are typically dependent on the number of cross-linkages, rather than molecular weight. The ability of silicone elastomers to swell makes them ideal thickeners for oil phases. The elastomers have a very smooth and soft feel when applied to skin or hair. They can also be used as delivery agents for fragrances, vitamins and other additives in cosmetic compositions. Suitable silicone elastomer blends or gels which are commercially available and suitable for inclusion in the composition of the invention and found to provide the enhanced stability are: Dow Corning® EL-8051 IN Silicone Organic Elastomer Blend [INCI Name: Isodecyl Neopentanoate (and) Dimethicone/Bis Isobutyl PPG-20 Crosspolymer], EL-8050 [INCI Name: Isododecane (and) Dimethicone/Bis-Isobutyl PPG 20 Crosspolymer], DC9040, DC9041, DC9045 (Dimethicone crosspolymer), DC9506, DC9509 (Dimethicone vinyl dimethicone crosspolymer) and Shin-Etsu KSG-15, KSG-16, KSG-17 (Dimethicone vinyl dimethicone crosspolymer). It is further preferred that the composition comprises from 5 to 50% by weight silicone elastomer.

Preferably, the cosmetically acceptable base is present preferably from 10 to 99.8%, more preferably from 50 to 99%, even more preferably from 60 to 85% and further more preferably from 65 to 80% by weight of the composition.

Preferably, the composition further comprises skin lightening agents. Examples of skin lightening agents that may be used in the composition include, 12-hydroxystearic acid, aloe extract, ammonium lactate, arbutin, azelaic acid, kojic acid, butyl hydroxy anisole, butyl hydroxy toluene, citrate esters, 3 diphenyl propane derivatives, 2, 5 dihydroxybenzoic acid and its derivatives, ellagic acid, fennel extract, gluco pyranosyl-1-ascorbate, gluconic acid, glycolic acid, green tea extract, hydroquinone, 4 hydroxyanisole and its derivatives, 4-hydroxy benzoic acid derivatives, hydroxycaprylic acid, lemon extract, linoleic acid, magnesium ascorbyl phosphate, mulberry root extract, 2,4 resorcinol derivatives, 3,5 resorcinol derivatives, salicylic acid, vitamins like vitamin B6, vitamin B12, vitamin C, vitamin A, a dicarboxylic acid, resorcinol derivatives, hydroxycarboxylic acid like lactic acid and their salts e.g. sodium lactate and mixtures thereof.

Preferably, the composition further comprises one or more sunscreens. Any sunscreen that can be suitably used with the base may be added. Both, UVA and UVB sunscreens may preferably be added.

The composition of the invention may preferably comprise a UV-A sunscreen which is a dibenzoylmethane or its derivatives. Preferred dibenzoylmethane derivatives are selected from 4-tert-butyl-4'-methoxydibenzoylmethane, 2-methyldibenzoylmethane, 4-methyl-dibenzoylmethane, 4-isopropyldibenzoyl-methane, 4-tert-butyldibenzoylmethane, 2,4-dimethyldibenzoylmethane, 2,5-dimethyldibenzoylmethane, 4,4'-diisopropyl-dibenzoylmethane, 2-methyl-5-isopropyl-4'-methoxydibenzoylmethane, 2-methyl-5-tert-butyl-4'-methoxy-dibenzoyl methane, 2,4-dimethyl-4'-methoxy dibenzoylmethane or 2,6-dimethyl-4-tert-butyl-4'-methoxy-dibenzoylmethane. The most preferred dibenzoylmethane derivative is 4-tert-butyl-4'-methoxydibenzoylmethane. The composition of the invention preferably comprises from 0.1 to 10%, more preferably from 0.2 to 5%, further more preferably from 0.4 to 3%, by weight dibenzoylmethane or a derivative thereof based on total weight of the composition and including all ranges subsumed therein.

The composition may also preferably comprise a UV-B organic sunscreen selected from the class of cinnamic acid, salicylic acid, diphenyl acrylic acid and derivatives thereof. Illustrative non-limiting example of UV-B sunscreens which are commercially available and useful for inclusion in the composition of the invention are Octisalate™, Homosalate™, NeoHelipan™, Octocrylene™, Oxybenzone™ or Parsol MCX™. The UV-B sunscreen is most preferably 2-ethyl-hexyl-4-methoxy cinnamate which is commercially available as Parsol MCX™. The UV-B organic sunscreen is preferably included in the composition from 0.1 to 10%, more preferably from 0.1 to 7% by weight of the composition. It has been observed that presence of an organic UV-B sunscreen like 2-ethyl-hexyl-4-methoxy cinnamate causes further rapid degradation of the UV-A dibenzoylmethane sunscreen in the presence of UV radiation. The presence of the rosmarinic acid ester compound is found to be very efficacious in stabilizing the composition even when UV-B sunscreens are present.

Useful inorganic sun-blocks are also preferably used in the present invention. These include, for example, zinc oxide, iron oxide, silica, such as fumed silica, and titanium dioxide.

The composition may further comprise preservatives to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts. Particularly preferred preservatives are phenoxyethanol, methyl paraben, propyl paraben, imidazolidinyl urea, sodium dehydroacetate, benzyl alcohol, alkane diols most preferably 1,2-octane diol and phenoxyethanol. The preservatives should be selected having regard for the use of the composition and possible incompatibility between the preservatives and other ingredients. Preservatives are preferably employed in amounts from 0.01% to 2% by weight of the composition.

A variety of other optional materials may be formulated into the compositions. These may include: antimicrobials such as 2-hydroxy-4,2',4'-trichlorodiphenylether (triclosan), 2,6-dimethyl-4-hydroxychlorobenzene, and 3,4,4'-trichlorocarbanilide, scrub and exfoliating particles such as polyethylene and silica or alumina; cooling agents such as menthol; skin calming agents such as aloe vera; and colorants.

In addition, the compositions may further comprise from 0 to 10% by weight of opacifiers and pearlizers such as ethylene glycol distearate, titanium dioxide or Lytron® 621 (Styrene/Acrylate copolymer); all of which are useful in enhancing the appearance or properties of the product.

Diluents other than water that may be used in the composition includes liquid or solid emollients, solvents, humectants, thickeners and powders. Examples of each of these types of vehicle, which can be used singly or as mixtures of one or more vehicles, are as follows:

Preferably, the composition comprises emollients. Examples of emollients that may be present include stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate.

Preferably, the composition comprises solvents such as ethyl alcohol, isopropanol, acetone, ethylene glycol monoethyl ether, diethylene glycol monobutyl ether, diethylene glycol monoethyl ether and mixtures thereof.

Advantageously, the composition may preferably comprise ingredients like bactericides, vitamins, anti-acne actives, anti-wrinkle, anti-skin atrophy and skin repair actives, skin barrier repair actives, non-steroidal cosmetic soothing actives, artificial tanning agents and accelerators, sebum stimulators, sebum inhibitors, anti-oxidants, protease inhibitors, skin tightening agents, anti-itch ingredients, hair growth inhibitors, 5-alpha reductase inhibitors, desquamating enzyme enhancers, anti-glycation agents and mixtures thereof.

The composition may preferably comprise powders like e.g. chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate and mixtures thereof.

The compositions of the present invention can comprise a wide range of other optional components. The CTFA Personal care Ingredient Handbook, Second Edition, 1992, which is incorporated by reference herein in its entirety, describes a wide variety of non-limiting personal care and pharmaceutical ingredients commonly used in the skin care industry, which are suitable for use in the compositions of the present invention. Examples include: antioxidants, binders, biological additives, buffering agents, colorants, thickeners, polymers, astringents, fragrance, humectants, opacifying agents, conditioners, pH adjusters, natural extracts, skin sensates, skin soothing agents, and skin healing agents.

The composition may also comprise one or more of the following ingredients e.g. chloroxylenol, zinc pyrithione (ZPT), creatine and creatinine.

The composition is preferably in the form of a wash-off or a leave-on composition, preferably a leave-on composition.

Wash-off composition preferably means composition which is intended/required to be removed from the body by washing with solvent preferably water after the application of the composition like e.g. hand wash composition and face wash composition.

Leave-on composition preferably means composition which is not required to be removed from the human body after the application of the composition like e.g. skin cream, body lotion, hand sanitizer and deodorants.

When the composition is in the form of a leave-on composition, the composition may be in the form of a deodorant, a hand sanitizer, a lotion, a cream and a body spray.

The composition of the invention may preferably comprise a conventional deodorant base as the cosmetically acceptable carrier. By a deodorant is meant a product in the stick, roll-on, or propellant medium which is used for personal deodorant benefit e.g. application in the under-arm area which may or may not contain anti-perspirant actives.

Deodorant compositions can generally be in the form of firm solids, soft solids, gels, creams, and liquids and are dispensed using applicators appropriate to the physical characteristics of the composition. Deodorant compositions which are delivered through roll-ons generally comprise a liquid carrier. Such liquid carrier can be hydrophobic or comprise a mixture of both hydrophilic and hydrophobic liquids. They may be in the form of an emulsion or a microemulsion. The liquid carrier or mixture of carriers often constitutes from 30 to 95% and in many instances from 40 to 80% by weight of the composition. Hydrophobic liquid carriers commonly can comprise one or more materials selected within the chemical classes of siloxanes, hydrocarbons, branched aliphatic alcohols, esters and ethers that have a melting point not higher than 25° C. and a boiling point of at least 100° C. Hydrophilic carrier liquids that can be employed in compositions herein commonly comprise water and/or a mono or polyhydric alcohol or water-miscible homologue. Other than this suitable other vehicle and component used for deodorant composition can be added.

The present invention also provides a method of cleaning or disinfecting a surface comprising the steps of applying the composition as disclosed above on to a surface in case of a leave-on composition. This method optionally comprises an additional step of at least partially removing the composition from the surface if it is in the form of a wash-off composition. Preferably, the step of at least partially removing the composition is carried out in less than 5 minutes after the step of applying the composition on to the substrate. Preferably, the method is non-therapeutic.

The present invention also provides an use of the composition as disclosed above for antimicrobial benefit. An antimicrobial benefit preferably means after application of the composition, the residual microbes on the surface is significantly less. The composition of the present invention provides improved antimicrobial benefits.

The present invention also provides an use of a composition as disclosed above for malodor benefits.

The present invention also provides an use of a composition as disclosed above for malodor benefits.

The present invention further provides a use of tetrahydroxypropyl ethylenediamine (THPE) in a composition comprising at least one compound selected from a biphenol as an antimicrobial efficacy enhancer Now the invention will be demonstrated in terms of examples. The following examples are just for illustration and in no way limits the scope of the present invention.

EXAMPLES

Malodour Assay Using Lead Acetate Paper:

The following tests were done to find out the efficacy of different compositions inside and outside the scope of the present invention:

The early morning saliva from different volunteer (5 samples) were pooled and centrifuged (Eppendorf refrigerated centrifuge 5810R at 6300 rcf/11.5 G) for 10 minutes. After that, the Supernatant which is saliva and the pellet—mixed bacterial pool (oral bacteria e.g. Streptococcus. mitis, Streptococcus. mutans, Nisseria. flava, Rothia. dentocariosa etc.,) was separated. The saliva was then filter sterilized by passing through the 50 mL conical 0.2 μm PES sterile filter (VWR lab products limited). The OD of total salivary bacterial pool culture was adjusted to 0.4 by spectrophotometer (Shimadzu UV Spectrophotometer—UV-1800) for higher pool of bacteria which is required for the assay. The assay was set up in a 96 well plate with respective culture control and DMSO control. The total reaction volume was 200 μL/well which comprises of the following:

45 μl 0.1% L-cysteine-HCl (Sigma, C1276)+TSB (Bacto, 211825, 30 g/L)+50 μL sterile Saliva+ 75 μL Culture+30 μL active (as per the weight % disclosed in the following table 2)+sterile distilled water.

Then the actives at desired concentration were added and the remaining volume was adjusted with sterile distilled water. After that, the wells were mixed well, and lead acetate filter was placed above the wells to capture the $H_2S$ released by the bacteria. The Plate was incubated overnight and checked for the darkening of the paper from the respective wells. Darker the spot more the $H_2S$ production and lighter the spot more the inhibition of $H_2S$ production. The intensity of the spots was measured using a LAB reader (Minolta spectrophotometer CM 2600D). The colour reading was expressed in LAB, L* defines lightness, A* denotes the red/green value and B* the yellow/blue value. Then ΔL, ΔA and ΔB is calculated using this formula ΔL=L control−L sample, ΔA=L control−L sample, AB=L control−L sample. The total colour difference which is expressed as ΔE is calculated using this formula ΔE= $\sqrt{(\Delta L)^2+(\Delta A)^2+(\Delta B)^2}$. Greater the ΔE value more the inhibition of $H_2S$ production. The total fold change of $H_2S$ inhibition over the control was calculated for the individual actives. The results are summarized below in Table 3.

TABLE 3

| Example No. | Composition (weight %) | Fold Change |
|---|---|---|
| A | 0.5 THPE | 0.9 ± 0.3 |
| B | 0.025 M | 1.6 ± 1.8 |
| C | 0.05 M | 1.5 ± 1.8 |
| D | 0.025 HM | 1.5 ± 1.8 |
| E | 0.05 HM | 0.89 ± 0.52 |
| 1 | 0.5 THPE + 0.025 M | 5.8 ± 0.5 |
| 2 | 0.5 THPE + 0.05 M | 6.0 ± 0.5 |
| 3 | 0.5 THPE + 0.025 HM | 6.0 ± 0.5 |
| 4 | 0.5 THPE + 0.05 HM | 6.4 ± 0.6 |

In the above table HM means a combination of honokiol and magnolol at 1:1 ratio which was purchased from World-Way Biotech Inc.®, China. In the same way 'M' means only honokiol. In this case Honokiol (98% pure) was purchased from World-Way Biotech Inc.®, China. In the above table 'THPE' means tetrahydroxypropyl ethylenediamine which was purchased from Sigma.

From the above table it is evident that the compositions within the scope of the present invention (Examples 1 to 4) provides synergistic effect e.g. for example A the fold change is (0.9±0.3) and for Example E the fold change is only 0.89±0.52. However, when Example A and E are combined i.e. Example 4, the resultant fold change is 6.4±0.6 which is much higher than the combined effect of Example A and E. The similar results can also be seen from other examples.

The invention claimed is:

1. An antimicrobial composition comprising;
    a. 0.1 to 10% by weight of tetrahydroxypropyl ethylenediamine (THPE); and,
    b. 0.001 to 10% by weight of at least one compound selected from a biphenol.

2. The antimicrobial composition as claimed in claim 1, wherein the biphenol comprises di-allyl substitution.

3. The antimicrobial composition as claimed in claim 2, wherein the di-allyl substitution is at the position 3-5' or 5-5' of the biphenol.

4. The antimicrobial composition as claimed in claim 3, wherein the biphenol is selected from honokiol and magnolol.

5. The antimicrobial composition as claimed in claim 1, additionally comprising niacinamide or its derivatives selected from picolinamide, isonicotinamide, N-cyclopropyl nicotinamide, and N-cyclopentyl nicotinamide.

6. The antimicrobial composition as claimed in claim 5, wherein the amount of niacinamide or its derivatives is in the range of 0.1 to 10% by weight.

7. The antimicrobial composition as claimed in claim 1, further comprising a cosmetically accepted base.

8. The antimicrobial composition as claimed in claim 1, wherein the composition is in the form of a leave-on composition.

9. The antimicrobial composition as claimed in claim 1, wherein the composition is in the form of a wash-off composition.

10. The antimicrobial composition as claimed in claim 8, wherein said leave-on composition includes lotion, cream, deodorants, hand sanitizer and body spray.

11. A method of disinfecting a surface comprising the step of applying on to the surface the antimicrobial composition as claimed in claim 1.

12. The method as claimed in claim 11, wherein the composition is in the form of a wash-off composition and wherein the method comprises an additional step of at least partially removing the composition.

13. A method of obtaining an antimicrobial benefit, comprising applying the antimicrobial composition of claim 1 to a surface, wherein after application of the antimicrobial composition, residual microbes on the surface are less than before application.

* * * * *